US010183864B2

(12) United States Patent
Vidjayacoumar et al.

(10) Patent No.: US 10,183,864 B2
(45) Date of Patent: Jan. 22, 2019

(54) PRODUCTION OF HYDROGEN GAS AND CALCIUM CARBONATE FROM FORMALDEHYDE

(71) Applicant: SABIC Global Technologies B.V., Bergen op Zoom (NL)

(72) Inventors: Balamurugan Vidjayacoumar, Thuwal (SA); Khalid Al-Bahily, Thuwal (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 47 days.

(21) Appl. No.: 15/503,510

(22) PCT Filed: Sep. 21, 2016

(86) PCT No.: PCT/IB2016/055639
§ 371 (c)(1),
(2) Date: Feb. 13, 2017

(87) PCT Pub. No.: WO2017/060788
PCT Pub. Date: Apr. 13, 2017

(65) Prior Publication Data
US 2017/0240420 A1 Aug. 24, 2017

Related U.S. Application Data

(60) Provisional application No. 62/239,553, filed on Oct. 9, 2015.

(51) Int. Cl.
*C01B 3/26* (2006.01)
*C01F 11/18* (2006.01)
(Continued)

(52) U.S. Cl.
CPC ............... *C01B 3/26* (2013.01); *B01J 27/26* (2013.01); *B01J 35/004* (2013.01); *C01F 11/18* (2013.01);
(Continued)

(58) Field of Classification Search
CPC .......... B01J 27/26; B01J 35/004; C01B 3/26; C01B 2203/0277; C01B 2203/1041;
(Continued)

(56) References Cited

U.S. PATENT DOCUMENTS 4,087,373 A * 5/1978 Reed, Jr. ................ C01B 3/22
252/373
2015/0086473 A1 3/2015 Yamaguchi et al. ....... 423/658.2

FOREIGN PATENT DOCUMENTS

WO    WO 2014204200    12/2014
WO    WO 2015003680    1/2015

OTHER PUBLICATIONS

Alderman et al., *Dalton Trans.* DOI:10.1039/c6dt03658a, 2016.
(Continued)

*Primary Examiner* — Amber R Orlando
*Assistant Examiner* — Syed T Iqbal
(74) *Attorney, Agent, or Firm* — Norton Rose Fulbright US LLP

(57) ABSTRACT

Disclosed is a method of producing hydrogen ($H_2$) gas and calcium carbonate from formaldehyde. The method includes combining an aqueous base, formaldehyde, and a transition metal complex having a coordination bond between a transition metal and a leaving group to form a homogeneous aqueous solution having a basic pH, wherein the leaving group dissociates from the transition metal complex in response to light and/or the basic pH of the solution, producing hydrogen ($H_2$) gas and formate or a salt thereof from the formaldehyde present in the homogeneous aqueous solution, and producing calcium carbonate using the formate or salt thereof as a carbon source.

19 Claims, 9 Drawing Sheets

(51) Int. Cl.
  *C07C 45/00*   (2006.01)
  *B01J 27/26*   (2006.01)
  *B01J 35/00*   (2006.01)
  *C07C 51/16*   (2006.01)
  *C07C 51/41*   (2006.01)

(52) U.S. Cl.
  CPC .............. *C07C 45/00* (2013.01); *C07C 51/16* (2013.01); *C07C 51/412* (2013.01); *C01B 2203/0277* (2013.01); *C01B 2203/1041* (2013.01); *C01B 2203/1047* (2013.01); *C01B 2203/1064* (2013.01); *C01B 2203/1088* (2013.01); *C01B 2203/1211* (2013.01)

(58) Field of Classification Search
  CPC .... C01B 2203/1047; C01B 2203/1064; C01B 2203/1088; C01B 2203/1211; C01F 11/18; C07C 45/00; C07C 51/16; C07C 51/412
  See application file for complete search history.

(56) References Cited

OTHER PUBLICATIONS

Bi et al., *International Journal of Hydrogen Energy* 33:2225-2232, 2008.
Fujita et al., *Angewandte Chemie* 54(31):9057-9060, 2015.
Geo Specialty Chemicals, "Calcium Formate Product Data", 2015. Retrieved from http://www.geosc.com/Assets/Files/Products-Docs/P-C-Product-Docs/Trimet-Products/CAF-TDS-US-Format on Nov. 30, 2016.
International Search Report and Written Opinion for PCT/IB2016/055639 dated Dec. 9, 2016.
Judd et al., *J. Appl. Chem. Biotechnol.*, 21:149-153, 1971.
Kapoor et al., *J. Phys. Chem.* 99:6857-6863, 1995.
Sleat et al., *Appl. Environ. Microbiol.* 47(4):884-885, 1984.
Suenobu et al., *Chem. Commun.* 51:1670-1672, 2015.
Wang et al., *Fuel* 140:267-274, 2015.

* cited by examiner

PRODUCTION OF HYDROGEN GAS AND CALCIUM CARBONATE FROM FORMALDEHYDE

CROSS REFERENCE TO RELATED APPLICATIONS

This application is a national phase application under 35 U.S.C. § 371 of International Application No. PCT/IB2016/055639 filed Sep. 21, 2016, which claims the benefit of priority of U.S. Provisional Patent Application No. 62/239,553, filed Oct. 9, 2015. The entire contents of each of the above-referenced disclosures are specifically incorporated herein by reference without disclaimer.

BACKGROUND OF THE INVENTION

A. Field of the Invention

The invention generally concerns a method for producing hydrogen gas ($H_2$) and calcium carbonate ($CaCO_3$) from formaldehyde. In particular, an aqueous basic composition containing formaldehyde and a transition metal complex having a coordination bond between a transition metal and a leaving group can produce hydrogen gas and formate or a salt thereof from the formaldehyde. The formate or salt thereof can then be used as a carbon source for the production of $CaCO_3$ and formaldehyde, the latter of which can be recycled to produce more hydrogen gas and $CaCO_3$.

B. Description of Related Art

There is increasing global demand for hydrogen gas. Conventional technology produces hydrogen from steam reforming of methane as shown in the equations (1) and (2) below. The major source of the methane is from natural gas:

(1)

(2)

Due to the depletion of fossil fuels, there is a necessity to find an alternative feedstock to meet the growing demand for hydrogen production globally.

As for calcium carbonate ($CaCO_3$), it finds many uses across a variety of industries. Some examples include its use in the (1) construction industry as a building material or in the production of cement, (2) oil industry as an additive to drilling fluids as a formation-bridging and filtercake-sealing agent, (3) food industry as a raw materials for refining sugar from sugar beet, (4) adhesive industry as an ingredient in adhesives, sealants, and decorating fillers, (5) paining industry as a paint extender, (5) medical industry as a calcium supplement or gastric antacid, or (6) pharmaceutical industry as a filler for tablets and other pharmaceutical dosage forms.

A variety of processes for producing hydrogen gas and calcium carbonate have been proposed. With respect to hydrogen gas production, some processes range from water-splitting, thermal dehydrogenation of formic acid, catalytic dehydrogenation of small organic molecules, or thermal dehydrogenation of amino-boranes and the like. Dehydrogenation of small organic molecules such as formic acid, methanol and formaldehyde has been attempted. Dehydrogenation of formic acid into hydrogen and carbon dioxide suffers in that the reaction is inefficient as formic acid has a low hydrogen content (about 4.4 wt. %). Further, the production of carbon dioxide can be problematic.

As for methanol, while it has a high hydrogen content (12.5 wt. %), the dehydrogenation process suffers in that the catalysts used to promote the dehydrogenation are sensitive to air and easily decompose. Further, methanol reforming is conducted at high temperatures (200° C.) and pressures (>25 bar), thereby limiting the scalability of the process.

With respect to formaldehyde, while there have been attempts to use formaldehyde in hydrogen production processes, the processes can require additional materials and/or use high temperatures, thereby making the processes inefficient and difficult to scale-up for mass hydrogen gas production. By way of example, International Application Publication No. WO 2014/204200 to Yoon et al. describes the dehydrogenation of methanol in the presence of formaldehyde using a palladium oxide on titanium dioxide photocatalyst to produce hydrogen. International Application Publication No. WO 2015/003680 to Prechtl et al. describes thermal process for generating hydrogen by heating formaldehyde-containing wastewater at 95° C. in the presence of a catalyst having a dimeric form of ruthenium with aromatic hydrocarbon ligands. Wang et al. in "Novel microbial synthesis of Cu doped $LaCoO_3$ photocatalyst and its high efficient hydrogen production from formaldehyde solution under visible light irradiation," *Fuel,* 2015, Vol. 140, pp. 267-274 describes preparation of a copper doped $LaCoO_3$ using microorganisms. Kapoor et al. in "Kinetics of Hydrogen Formation from Formaldehyde in Basic Aqueous Solutions," *Journal of Physical Chemistry,* 1995, Vol. 99 describes the kinetics of thermal generation of hydrogen from solutions of formaldehyde in the form of HCHO, with an increase in hydrogen production observed by an increase in reaction temperatures. Notably, Kapoor et al. also explains that hydrogen production is from HCHO and trioxane and is not from para-formaldehyde.

In addition to the inefficiencies of the systems discussed above, photocatalytic attempts to produce hydrogen from aqueous formaldehyde solutions have typically relied on water splitting to generate electron holes that oxidize the formaldehyde to formic acid. Subsequent photo-oxidation of the formic acid produces hydrogen and carbon dioxide through a multi-step process shown in equations (3) through (9) below.

(3)

(4)

(5)

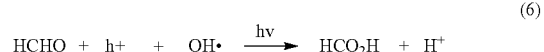

(6)

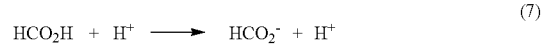

(7)

(8)

(9)

Regarding calcium carbonate production, the majority of calcium carbonate is extracted from the earth through mining or quarrying operations. For chemical synthesis, the conventional process includes mixing water with calcium oxide to produce a calcium hydroxide solution. Carbon dioxide is then passed through the solution to precipitate calcium carbonate.

SUMMARY OF THE INVENTION

A discovery has been made that provides a solution to the inefficiencies currently seen with producing hydrogen ($H_2$) gas. This discovery also provides an alternative process for producing calcium carbonate. Both of these materials can be obtained from formaldehyde as a starting point. In particular, the discovery is premised on the use of a homogeneous system that includes an aqueous basic solution having a transition metal complex catalyst and formaldehyde, both of which are partially or fully solubilized in the basic solution. Formate (and salt forms thereof, e.g., sodium formate) and hydrogen gas can be produced directly from the formaldehyde. The formate or salt thereof can then be used as a carbon source for producing calcium carbonate by (1) reacting the formate or salt thereof with calcium hydroxide ($Ca(OH)_2$) to produce calcium formate ($Ca(HCOO)_2$) and (2) converting $Ca(HCOO)_2$ to calcium carbonate ($CaCO_3$) and formaldehyde. The produced formaldehyde can then be recycled and used to produce more hydrogen gas and calcium carbonate, thereby increasing the efficiency of the process. Notably, the hydrogen production process of the present invention can be operated at reduced temperatures (e.g., 0° C. to less than 50° C. or preferably at room temperature conditions such as 15° C. to 30° C. or 20° C. to 25° C.) and can limit or avoid the production of undesired by-products such as carbon dioxide ($CO_2$). Without wishing to be bound by theory, it is believed that the efficiency of the process of the present invention occurs due to the fact that the production of $H_2$ and formate occurs in the homogeneous phase of the reaction mixture. Still further, the catalysts that can be used in the context of the present invention can range from light activated catalysts or catalysts that are activated in a basic pH environment, or both. The catalysts that can be used do not require the presence of expensive noble metals that are typically used in hydrogen production reactions, thereby further increasing the efficiency of the present invention from a cost-savings perspective (although such noble metals can be used with the processes and catalysts of the present invention if so desired).

In one aspect of the invention, a method of producing hydrogen gas (also referred to as $H_2$, $H_2$ gas, hydrogen, throughout the specification) and calcium carbonate is described. The method can include combining an aqueous base, formaldehyde (e.g., para-formaldehyde, hydrated formaldehyde, or a combination thereof), and a transition metal complex having a coordination bond between a transition metal and a leaving group to form a homogeneous aqueous solution having a basic pH to produce hydrogen and formate or a salt thereof from the formaldehyde present in the homogeneous aqueous solution. In some embodiments, the formaldehyde is the produced from the oxidation of methanol. The molar ratio of formaldehyde to base (e.g., NaOH, KOH, preferably NaOH) is equal to or less than 2:1, preferably equal to or less than 1.5:1, more preferably equal to or less than 1.2:1, even more preferably from 0.5:1 to 1.5:1, or most preferably from 1:1 to 1.3:1. The formaldehyde and the transition metal complex are fully solubilized in the homogeneous aqueous solution. The produced formate or salt thereof can then be used as a carbon source for the production of $CaCO_3$. To produce $CaCO_3$, the formate or salt thereof can be reacted with calcium hydroxide ($Ca(OH)_2$) to produce calcium formate ($Ca(HCOO)_2$). This production of calcium formate step can be performed at temperatures of greater than 0° C. to 400° C., preferably from greater than 0° C. to less than 50° C., more preferably from 10° C. to 40° C., even more preferably from 15° C. to 30° C., and most preferably from 20° C. to 25° C. Calcium carbonate and formaldehyde can then be produced from the calcium formate. This production of calcium carbonate step can be performed at a temperature of greater than 0° C. to 400° C., preferably 200° C. to 400° C., more preferably 250° C. to 350° C., or most preferably around 300° C. The formaldehyde produced from calcium formate can be recycled and used in the further production of hydrogen and formate. Reacting the formate or salt thereof with calcium hydroxide can produce, in addition to calcium formate, the same aqueous base originally present in the homogeneous aqueous solution (e.g., NaOH), which can then be recycled and used in the production of hydrogen and formate. In the production of hydrogen and formate or a salt thereof from formaldehyde in the homogeneous aqueous solution, the leaving group dissociates from the transition metal complex in response to light and/or the basic pH of the solution at a mild temperature (e.g., temperature of the mixture ranges from greater than 0° C. to less than 50° C., preferably from 10° C. to 40° C., more preferably from 15° C. to 30° C., and most preferably from 20° C. to 25° C.). A hydroxide ion can replace the leaving group to form a transition metal-hydroxyl coordination bond to form a transition metal complex having a transition metal-hydroxyl coordination bond, which in turn can react with the formaldehyde to produce the hydrogen and formate or salt thereof. The transition metal complex can include iron (Fe), ruthenium (Ru), iridium (Ir), copper (Cu), or silver (Ag) or a combination thereof. In one instance, the transition metal complex is an Fe(II) complex that has a leaving group that dissociates from the transition metal complex in response to light (e.g., sunlight, artificial light, or a combination thereof). A non-limiting example of such an iron complex is ferricyanide ($Fe(CN)_6)^{4-}$) with a cyano group ($CN^-$) being the leaving group. Non-limiting examples of artificial light include a xenon lamp, a fluorescent light, an LED light, an incandescent light, an ultraviolet (UV) light, or any combination thereof. In another aspect of the invention, the transition metal complex includes a leaving group that dissociates in response to the pH of the solution. The leaving group can be any group that is capable of dissociating under basic conditions (e.g., pH 8 to 14, 10 to 14, or 12 to 14). Non-limiting examples of such leaving groups are water ($H_2O$), ammonia ($NH_3$), cyanide ($CN^-$), thiocyanate ($SCN^-$), carbonate ($CO_3^-$), bicarbonate ($HCO_3^-$), a halide (e.g., fluoride ($F^-$), chloride ($Cl^-$), bromide ($Br^-$), iodide ($I^-$), or astatide ($At^-$)) or combinations thereof. In a preferred aspect, the leaving group is chloride ion.

In some aspects of the invention, a homogeneous aqueous solution having a basic pH and capable of producing hydrogen and calcium carbonate is disclosed. The composition can include the aqueous base, formaldehyde, and a transition metal complex having a coordination bond between a transition metal and a leaving group described herein. As previously described, the leaving group is capable of dissociating from the transition metal complex in response to light and/or the basic pH of the solution.

In another aspect of the invention, a system for producing hydrogen and calcium carbonate from formaldehyde is described. The system can include a container comprising the homogeneous aqueous solution described throughout the specification; and, optionally, a light source for illuminating the aqueous solution. The container can include a transparent portion, an opaque portion or both. The light source can be sunlight and/or an artificial light source (e.g., xenon lamp, a florescent light, an LED light, an incandescent light, an ultraviolet (UV) light, or any combination thereof).

Also disclosed in the context of the present invention are embodiments 1-53. Embodiment 1 is a method of producing hydrogen and calcium carbonate, the method comprising: (a) combining an aqueous base, formaldehyde, and a transition metal complex having a coordination bond between a transition metal and a leaving group to form a homogeneous aqueous solution having a basic pH, wherein the leaving group dissociates from the transition metal complex in response to light and/or the basic pH of the solution; (b) producing hydrogen ($H_2$) gas and formate or a salt thereof from the formaldehyde present in the homogeneous aqueous solution; and (c) producing $CaCO_3$ using the formate or salt thereof as a carbon source. Embodiment 2 is the method of embodiment 1, wherein step (c) comprises: (i) producing calcium formate ($Ca(HCOO)_2$) by reacting the formate or salt thereof with calcium hydroxide ($Ca(OH)_2$); and (ii) producing $CaCO_3$ and formaldehyde from the $Ca(HCOO)_2$. Embodiment 3 is the method of embodiment 2, wherein aqueous base is produced in step (c)(i) and recycled and used in steps (a) and (b). Embodiment 4 is the method of any one of embodiments 2 to 3, wherein the formaldehyde from step (c)(ii) is recycled and used in steps (a) and (b). Embodiment 5 is the method of any one of embodiments 1 to 4, wherein steps (a) and/or (b) are each performed at a temperature from greater than 0° C. to less than 50° C., preferably from 10° C. to 40° C., more preferably from 15° C. to 30° C., and most preferably from 20° C. to 25° C. Embodiment 6 is the method of any one of embodiments 1 to 5, wherein a hydroxide ion replaces the leaving group to form a transition metal-hydroxyl coordination bond, and wherein the transition metal complex having the transition metal-hydroxyl coordination bond reacts with the formaldehyde to produce the hydrogen and formate or salt thereof. Embodiment 7 is the method of any one of embodiments 1 to 6, wherein the transition metal is iron (Fe), ruthenium (Ru), iridium (Ir), copper (Cu), or silver (Ag). Embodiment 8 is the method of embodiment 7, wherein the transition metal complex is an Fe complex, preferably an Fe(II) complex. Embodiment 9 is the method of embodiment 7, wherein the transition metal complex is a Ru complex, preferably a Ru(III) complex. Embodiment 10 is the method of embodiment 7, wherein the transition metal complex is an Ir complex, preferably an Ir(III) complex. Embodiment 11 is the method of embodiment 7, wherein the transition metal complex is a Cu complex, preferably a Cu(I) complex. Embodiment 12 is the method of embodiment 7, wherein the transition metal complex is an Ag complex, preferably an Ag(I) complex. Embodiment 13 is the method of any one of embodiments 1 to 12, wherein the leaving group dissociates from the transition metal complex in response to light. Embodiment 14 is the method of embodiment 13, wherein the leaving group is a cyano group ($CN^-$). Embodiment 15 is the method of embodiment 14, wherein the transition metal complex is ferricyanide ($Fe(CN)_6^{4-}$) or a salt thereof. Embodiment 16 is the method of any one of embodiments 13 to 15, wherein the light is sunlight or artificial light, or a combination thereof. Embodiment 17 is the method of embodiment 16, wherein the artificial light is from a xenon lamp, a fluorescent light, an LED light, an incandescent light, an ultraviolet (UV) light, or any combination thereof. Embodiment 18 is the method of any one of embodiments 1 to 17, wherein the leaving group dissociates from the transition metal in response to the basic pH of the solution. Embodiment 19 is the method of embodiment 18, wherein the leaving group is a halide. Embodiment 20 is the method of embodiment 19, wherein the halide is fluoride ($F^-$), chloride ($Cl^-$), bromide ($Br^-$), iodide ($I^-$), or astatide ($At^-$), preferably $Cl^-$. Embodiment 21 is the method of any one of embodiments 1 to 20, wherein the molar ratio of formaldehyde to base is equal to or less than 2:1, preferably equal to or less than 1.5:1, more preferably equal to or less than 1.2:1, even more preferably from 0.5:1 to 1.5:1, or most preferably from 1:1 to 1.3:1. Embodiment 22 is the method of any one of embodiments 1 to 21, wherein the formaldehyde is para-formaldehyde, hydrated formaldehyde, or a combination thereof. Embodiment 23 is the method of any one of embodiments 1 to 22, wherein the formaldehyde is produced from methanol by oxidation of the methanol. Embodiment 24 is the method of any one of embodiments 1 to 23, wherein the base is NaOH. Embodiment 25 is the method of any one of embodiments 1 to 24, wherein the homogeneous aqueous solution has a pH from 8 to 14, preferably 10 to 14, and most preferably 12 to 14. Embodiment 26 is the method of any one of embodiments 1 to 25, wherein an external bias is not used to produce the hydrogen and formate or salt thereof. Embodiment 27 is the method of any one of embodiments 1 to 26, wherein the formaldehyde and the transition metal complex are fully solubilized in the homogeneous aqueous solution.

Embodiment 28 is a homogeneous aqueous solution having a basic pH and being capable of producing hydrogen ($H_2$) gas and calcium carbonate ($CaCO_3$), the composition comprising an aqueous base, formaldehyde, and a transition metal complex having a coordination bond between a transition metal and a leaving group, wherein the leaving group dissociates from the transition metal complex in response to light and/or the basic pH of the solution. Embodiment 29 is the homogeneous aqueous solution of embodiment 28, wherein the transition metal is iron (Fe), ruthenium (Ru), iridium (Ir), copper (Cu), or silver (Ag). Embodiment 30 is the homogeneous aqueous solution of embodiment 29, wherein the transition metal complex is an Fe complex, preferably an Fe(II) complex. Embodiment 31 is the homogeneous aqueous solution of embodiment 29, wherein the transition metal complex is a Ru complex, preferably a Ru(III) complex. Embodiment 32 is the homogeneous aqueous solution of embodiment 29, wherein the transition metal complex is an Ir complex, preferably an Ir(III) complex. Embodiment 33 is the homogeneous aqueous solution of embodiment 29, wherein the transition metal complex is a Cu complex, preferably a Cu(I) complex. Embodiment 34 is the homogeneous aqueous solution of embodiment 29, wherein the transition metal complex is an Ag complex, preferably an Ag(I) complex. Embodiment 35 is the homogeneous aqueous solution of any one of embodiments 28 to 34, wherein the leaving group dissociates from the transition metal complex in response to light. Embodiment 36 is the homogeneous aqueous solution of embodiment 35, wherein the leaving group is $CN^-$. Embodiment 37 is the homogeneous aqueous solution of embodiment 36, wherein the transition metal complex is ferricyanide ($Fe(CN)_6^{4-}$) or a salt thereof. Embodiment 38 is the homogeneous aqueous solution of any one of embodiments 35 to 37, wherein the light is sunlight or artificial light, or a combination thereof. Embodiment 39 is the homogeneous aqueous solution of embodiment 38, wherein the artificial light is from a xenon lamp, a fluorescent light, an LED light, an incandescent light, an ultraviolet (UV) light, or any combination thereof. Embodiment 40 is the homogeneous aqueous solution of any one of embodiments 28 to 34, wherein the leaving group dissociates from the transition metal in response to the basic pH of the solution. Embodiment 41 is the homogeneous aqueous solution of embodiment 40, wherein the leaving group is a halide. Embodiment 42 is the homogeneous aqueous solution of embodiment 41, wherein the halide is fluoride (F⁻), chloride (Cl⁻), bromide (Br⁻), iodide (I⁻), or astatide (At⁻), preferably Cl⁻. Embodiment 43 is the homogeneous aqueous solution of any one of embodiments 28 to 42, wherein the molar ratio of formaldehyde to base is equal to or less than 2:1, preferably equal to or less than 1.5:1, more preferably equal to or less than 1.2:1, even more preferably from 0.5:1 to 1.5:1, or most preferably from 1:1 to 1.3:1. Embodiment 44 is the homogeneous aqueous solution of embodiments 28 to 43, wherein the formaldehyde is para-formaldehyde, hydrated formaldehyde, or a combination thereof. Embodiment 45 is the homogeneous aqueous solution of any one of embodiments 28 to 44, wherein the base is NaOH. Embodiment 46 is the homogeneous aqueous solution of any one of embodiments 28 to 45, wherein the homogeneous aqueous solution has a pH from 8 to 14, preferably 10 to 14, and most preferably 12 to 14. Embodiment 47 is the homogeneous aqueous solution of embodiments 28 to 46, wherein the formaldehyde and the transition metal complex are fully solubilized in the homogeneous aqueous solution.

Embodiment 48 is a system for producing hydrogen ($H_2$) gas and calcium carbonate ($CaCO_3$) from formaldehyde, the system comprising: (a) a container comprising the homogeneous aqueous solution of any one of embodiments 28 to 47; and (b) optionally, a light source for illuminating the aqueous solution. Embodiment 49 is the system of embodiment 48, wherein the light source is sunlight or an artificial light source, or a combination thereof. Embodiment 50 is the system of embodiment 49, wherein the artificial light source is a xenon lamp, a florescent light, an LED light, an incandescent light, an ultraviolet (UV) light, or any combination thereof. Embodiment 51 is the system of any one of embodiments 48 to 50, wherein the container comprises a transparent portion. Embodiment 52 is the system of any one of embodiments 48 to 50, wherein the container comprises an opaque portion. Embodiment 53 is the system of any one of embodiments 49 to 53, wherein the system does not include an external bias to produce hydrogen or $CaCO_3$.

The following includes definitions of various terms and phrases used throughout this specification.

The term "homogeneous" is defined as a reaction equilibrium in which the catalysts reactants, and products are all or substantially all in the same phase (e.g., the catalysts, reactants and products are fully dissolved or substantially dissolved in the basic aqueous medium).

"Formaldehyde" as used herein includes gaseous, liquid and solid forms of formaldehyde. "Formaldehyde" includes its aldehyde form ($CH_2O$), its hydrated form (methanediol), and its para-formaldehyde form of

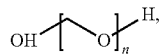

where n can be up to 100.

The "turn over number" or "TON," as used herein, means the number of moles of substrate that a mole of catalyst converts in the timeframe of the experiment or before being deactivated. TON is calculated as the number of millimoles of formaldehyde, divided by the number of moles of catalyst unless otherwise indicated.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having," in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the catalysts of the present invention are their abilities to catalyze hydrogen production from formaldehyde.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

or a basic pH (B) is used to disassociate the leaving group from the transition metal complex.

Figure 2:
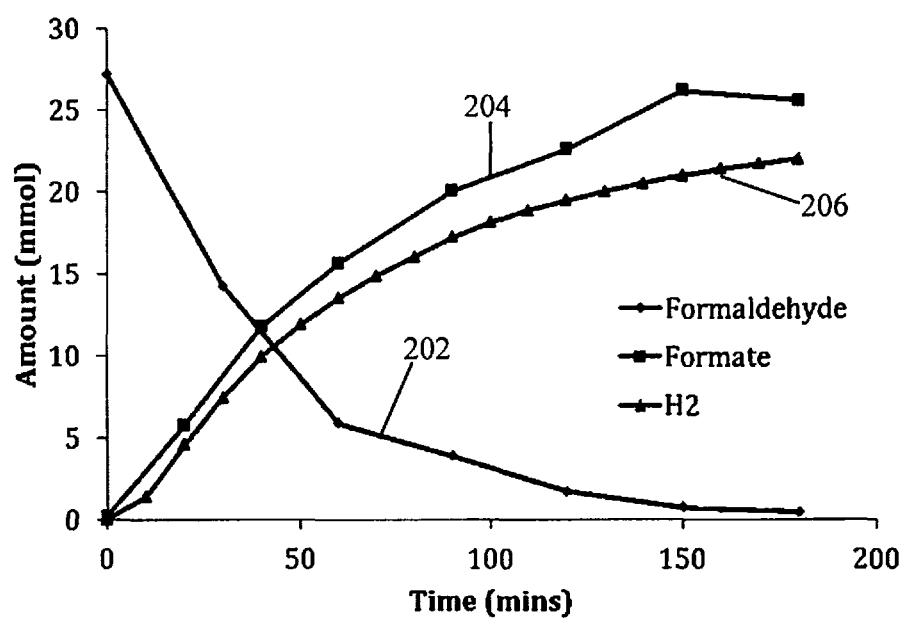

FIG. 2 are graphs of the amount of products formed or consumed over time during irradiation.

Figure 3:
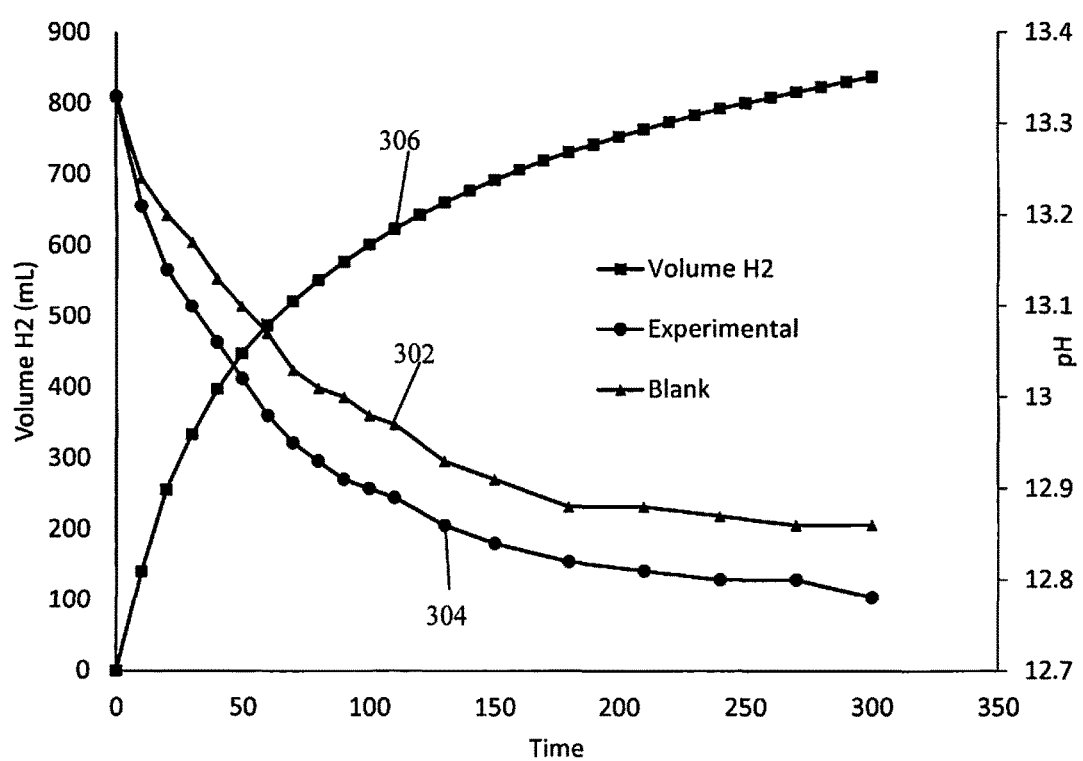

FIG. 3 are graphs of the hydrogen production and change of pH of the non-catalyzed reaction and the catalyzed reaction over time.

Figure 4:
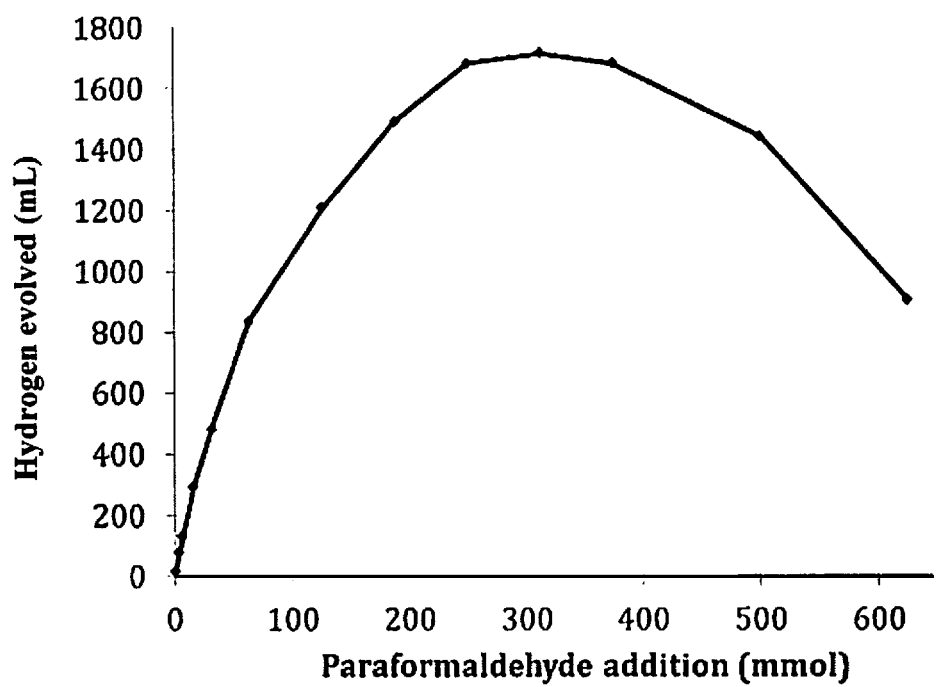

FIG. 4 is a graph of the change of hydrogen evolution versus the amount of p-formaldehyde added at a constant amount of NaOH.

Figure 5:
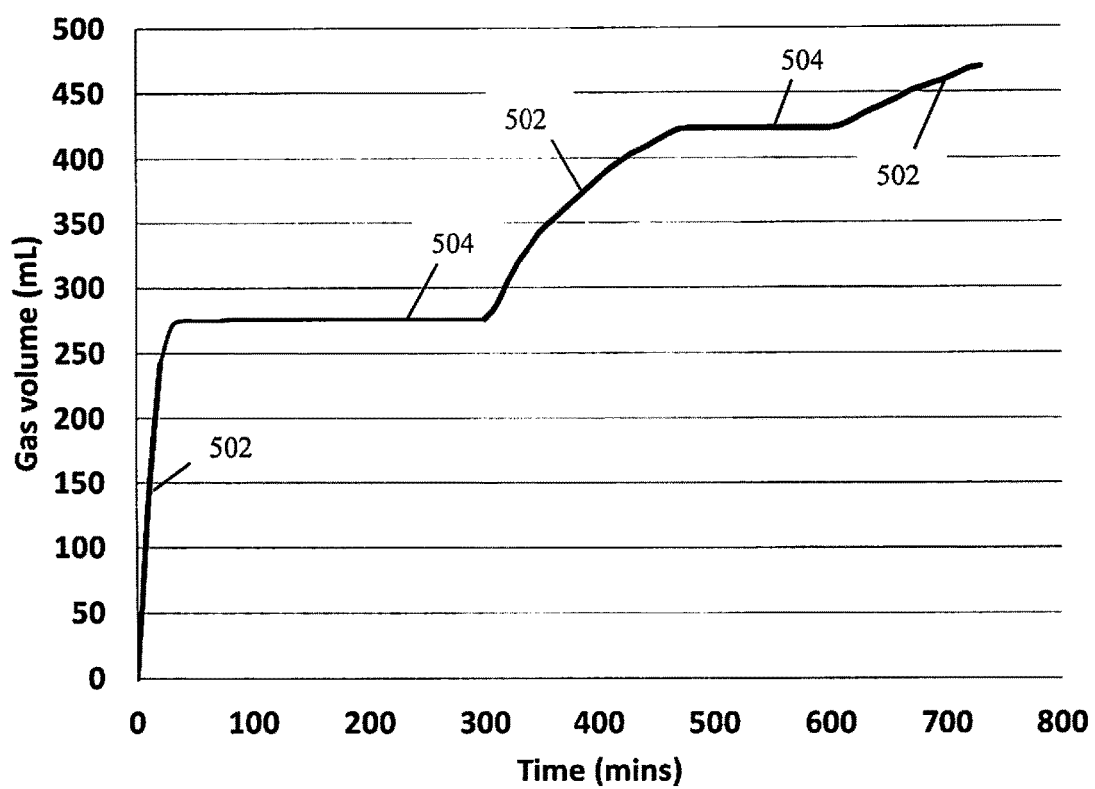

FIG. 5 is a graph of the effect of illumination on hydrogen evolution from ferrocyanide catalysis over time.

Figure 6:
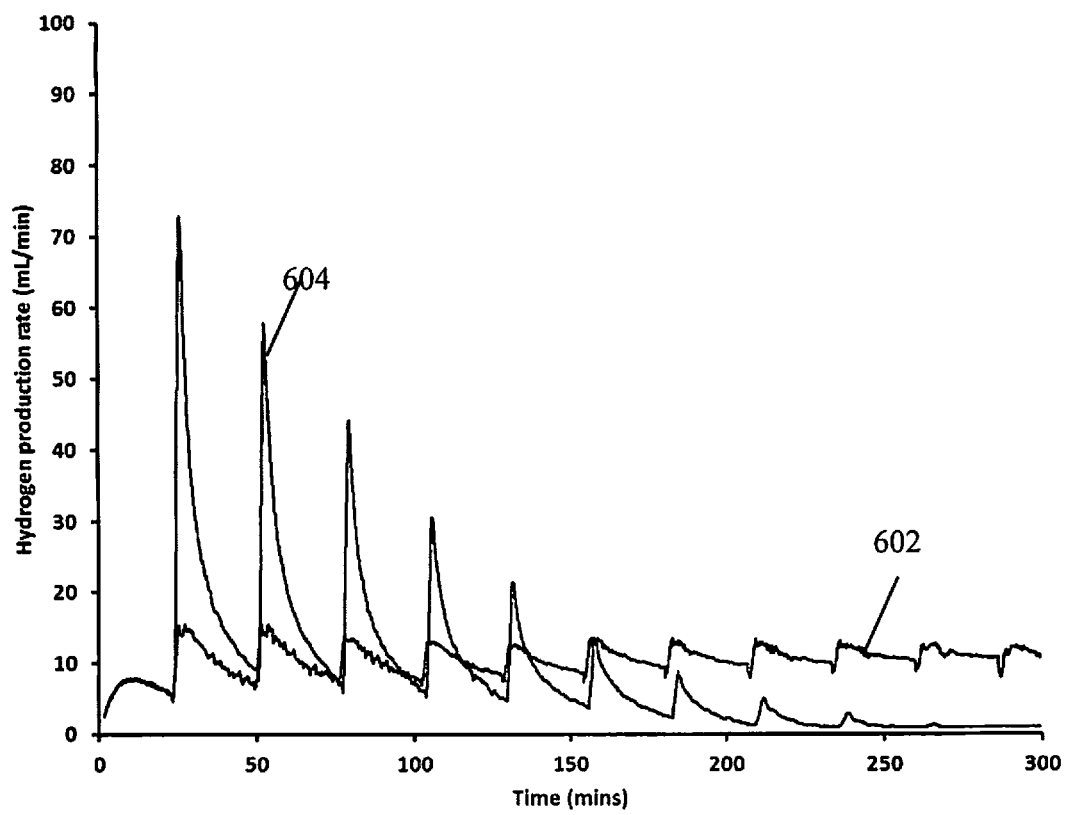

FIG. 6 are graphs of the hydrogen flow in ml/min versus time in minutes at various p-formaldehyde and NaOH concentrations.

Figure 7:
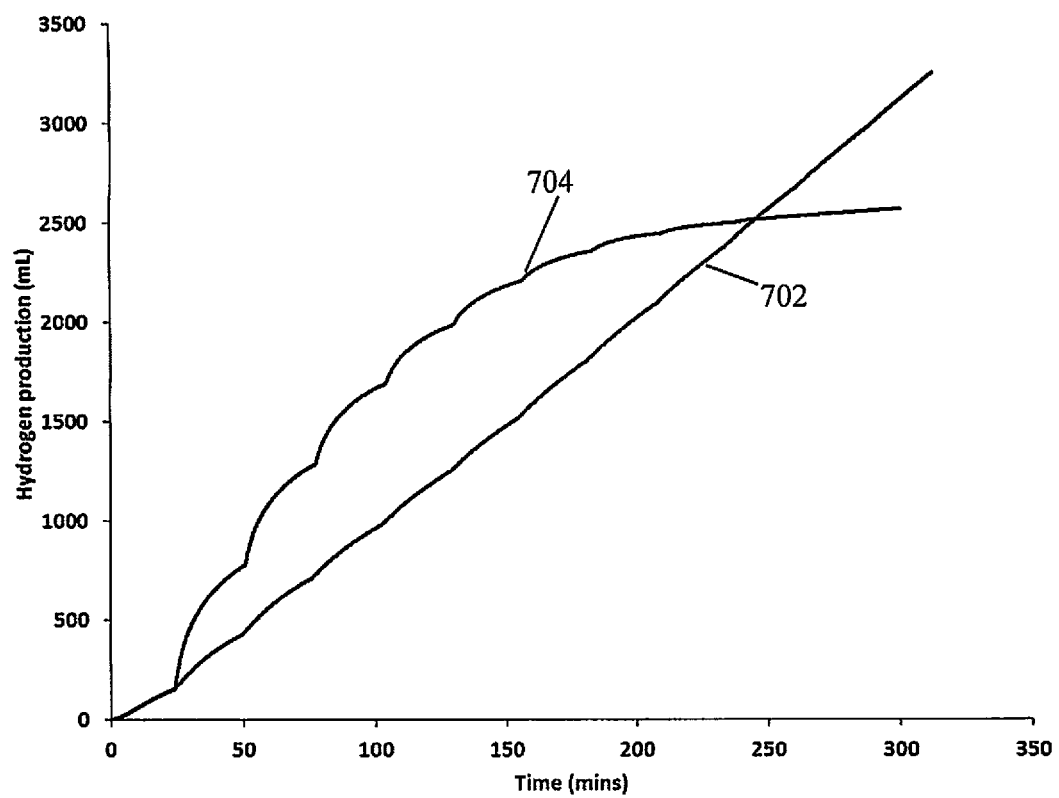

FIG. 7 are graphs of the hydrogen production versus time in minutes at various p-formaldehyde and NaOH concentrations.

Figure 8:
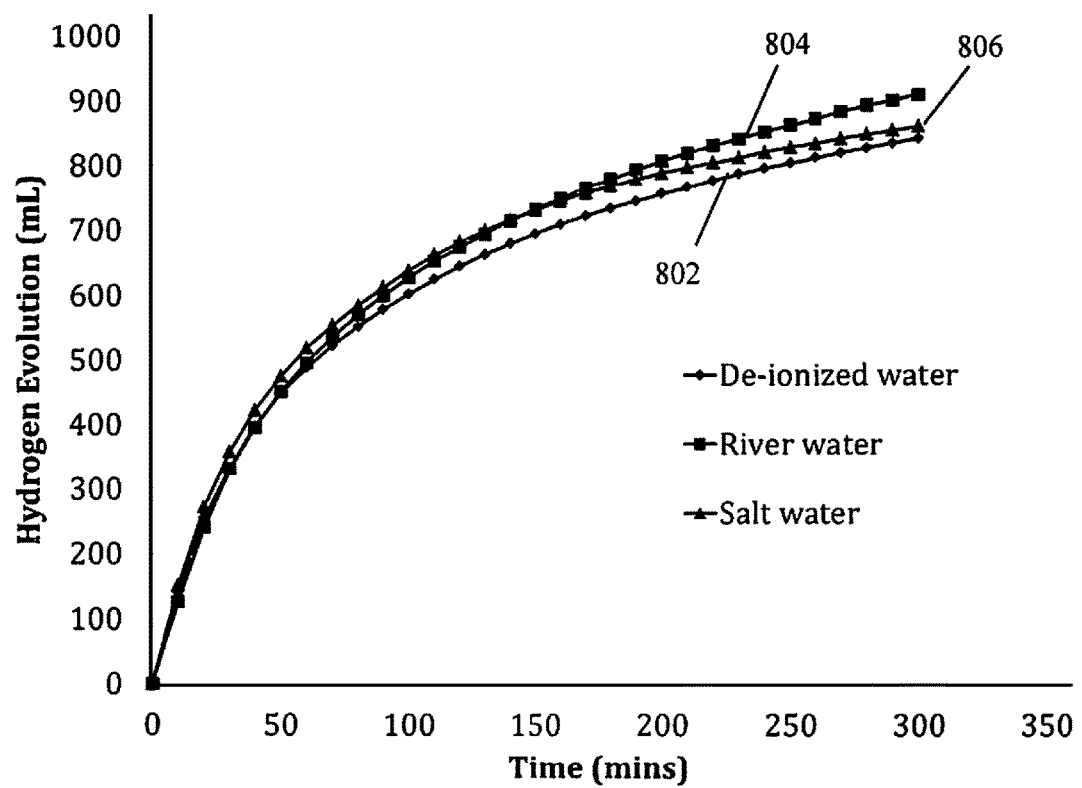

FIG. 8 are graphs of hydrogen production in mL versus time in min of the production of hydrogen using various types of water.

Figure 9:
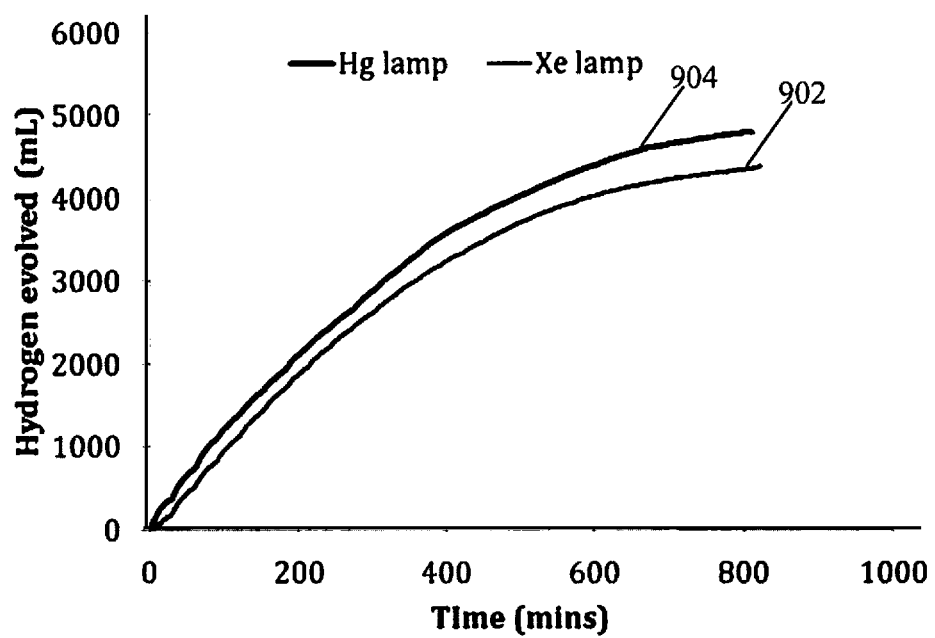

FIG. 9 are graphs of hydrogen evolution versus time using different light sources.

While the invention is susceptible to various modifications and alternative forms, specific embodiments thereof are shown by way of example in the drawings and may herein be described in detail. The drawings may not be to scale.

DETAILED DESCRIPTION OF THE INVENTION

The present invention provides for an efficient and scalable process for producing hydrogen gas and calcium carbonate from formaldehyde. The process includes combining an aqueous base, formaldehyde, and a transition metal complex catalyst having a coordination bond between a transition metal and a leaving group to form a homogeneous aqueous solution. In response to either light or to the basic pH of the solution, the leaving group can dissociate from the transition metal complex and can be replaced with a hydroxide ion to form a transition metal-hydroxyl coordination bond. The resulting transition metal complex can react with formaldehyde to produce hydrogen and formate or a salt thereof. As illustrated in non-limiting embodiments in the examples, this process can have large turn-over numbers, be operated at relatively low temperatures (e.g., greater than 0° C. to 50° C., preferably room temperatures such as 15° C. to 30° C. or more preferably 20° C. to 25° C.) and under a variety of conditions, thereby allowing for the efficient and scalable production of hydrogen gas and formate (and salt forms thereof). The produced formate (or a salt thereof such as sodium formate) can then be used as a carbon source in the production of calcium carbonate and/or additional formaldehyde by reacting the formate with calcium hydroxide ($Ca(OH)_2$ to form calcium formate ($Ca(CHOO)_2$). Calcium formate can then be converted into calcium carbonate and additional formaldehyde, the latter of which can be recycled. In addition to the low temperature processing conditions, the process of the present invention can limit or even avoid the production of by-products such as carbon dioxide ($CO_2$).

The below reaction scheme A provides a non-limiting illustration of a process of the present invention:

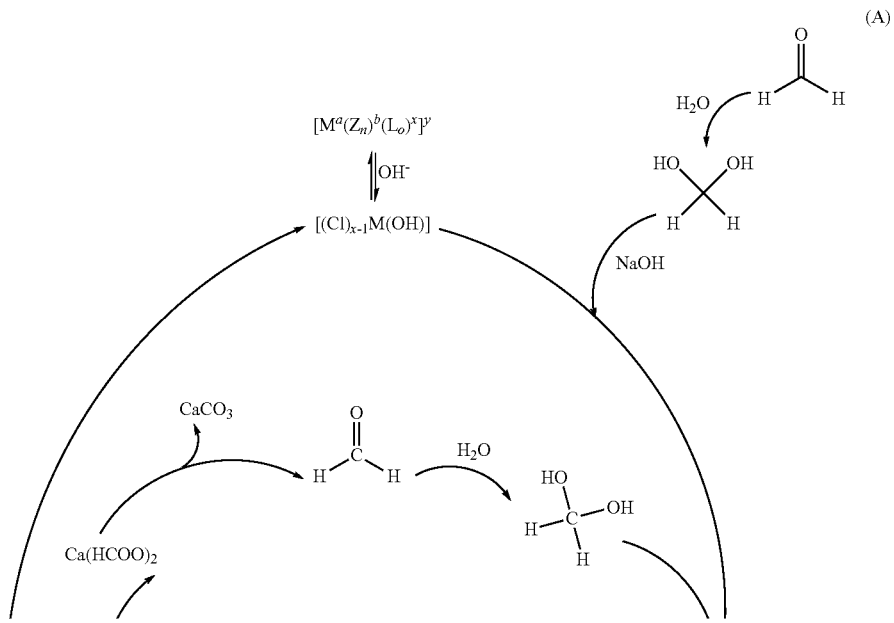

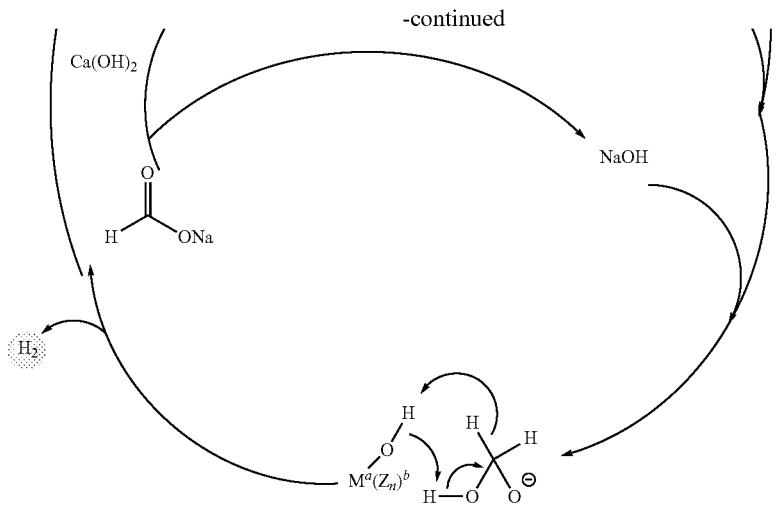

where M is a transition metal having a charge a, Z is a ligand bonded to the metal with a charge of b, L is a leaving group with a charge of x, a is a positive integer from 0 to 6, preferably 0 to 3, b is an negative integer from 0 to −5, x is a negative integer from −1 to −2, y is the total charge of the transition metal complex, and n, o, and p are the atomic ratios of Z, L and OH relative to M, where n is 0 to 6, o is 1 to 3, p is 1, and y is 0, −1, −2, −3, −4, −5, or −6. In a preferred embodiment, y is 0.

These and other non-limiting aspects of the present invention are discussed in further detail in the following sections.

A. Transition Metal Complex Catalyst

In some instances, a transition metal complex having a coordination bond between the transition metal and a leaving group acts as a catalyst for the production of formate and $H_2$ from formaldehyde. The transition metal complex can undergo a reversible dissociation reaction of at least one leaving group. Without wishing to be bound by theory, it is believed that the dissociation of at least one leaving group can produce a transient electrophilic species. A non-limiting example of a transition metal complex catalyst undergoing a dissociation reaction is shown in equation (10) below:

$$[M^a(Z_n)^b(L_o)^x]^y \leftrightarrow [M^a(Z_n)^b]^y + (L_o)^x \qquad (10)$$

where M is a transition metal having a charge a, Z is one or more ligands bonded to the metal with a total charge of b, L is one or more leaving group with total charge of x, and a is a positive integer from 0 to 6, preferably 0 to 3, b is an negative integer from 0 to −5, x is a negative integer from −1 to −2, y is the total charge of the transition metal complex, and n and o are the atomic ratio relative to M, where n ranges from 0 to 6 and o ranges from 1 to 3. In some instances y is 0, −1, −2, −3, −4, −5, or −6.

The transition metal complex can react with nucleophiles in the reaction mixture, for example, hydroxide ion as shown in equation (11) below.

$$[(M)^a(Z_n)^b(L_o)^x]^y + (OH^-)_p \leftrightarrow [(M)^a(Z_n)^b(OH^-)_p]^y \qquad (11)$$

where M is a transition metal having a charge a, Z is one or more ligands bonded to the metal with a total charge of b, L is one or more leaving group with total charge of x, and a is a positive integer from 0 to 6, preferably 0 to 3, b is an negative integer from 0 to −5, x is a negative integer from −1 to −2, y is the total charge of the transition metal complex, and n, o, and p are the atomic ratio relative to M, where n is ranges from 0 to 6, o ranges from 1 to 3, and p ranges from 0 to 1. In some instances y is 0, −1, −2, −3, −4, −5, or −6.

Without wishing to be bound by theory, it is believed that the $[(M)^a(Z_n)^b(OH^-)_p]^y$ species can react with small organic molecules (e.g., formaldehyde in either intact or hydrated form), followed by reductive elimination of hydrogen and consequent formation of the formate anion. Alternatively, the partly deprotonated form of methanediol ($CH_2(OH)_2$), as obtained from the attack of hydroxide ion top-formaldehyde, may also directly coordinate to the $[(M)^a(Z_n)^b(OH^-)_p]^y$ intermediate to form the same species.

In some instances, the transition metal in the transition metal complex catalyst can be, for example, iron (Fe), ruthenium (Ru), iridium (Ir), or silver (Ag). Preferably, the transition metal is Fe(II), Ru(III), Ir(III), Cu(I), or Ag(I). In some instances, the leaving group (L) can be from two general categories: (1) leaving groups that dissociate from the transition metal complex in response to light and (2), leaving groups that dissociate from the transition metal complex in response to the basic pH of the solution. The former category of leaving groups can include, for example, $CN^-$. The latter category can include, for example, halides, including fluoride ($F^-$), chloride ($Cl^-$), bromide ($Br^-$), iodide ($I^-$), or astatide ($At^-$). Ligand Z can be the same or different than leaving group L. In some embodiments, Z can be an inorganic ligand, an organic ligand or both. Non-limiting examples of organic groups include aromatic groups, a cyano group, a substituted cyano group, an acetate group, a thiocyanate group, an aminidate group, a nitrate group, or combinations thereof. Non-limiting examples of inorganic groups include a halide, phosphate, or both. In some complexes Z is not necessary (e.g., when M has a charge of +1).

In some instances, the transition metal complex contains iron and has a cyano ($CN^-$) leaving group. The iron containing catalyst can be a saturated 18-electron complex with Fe(II) in an octahedral, strong ligand-field. The iron containing catalyst can undergo a reversible dissociation reaction of at least one leaving group upon irradiation with visible light. Without wishing to be bound by theory it is believed that the dissociation of at least one leaving group can produce a transient penta-coordinated 16-electron species isolobal with an organic carbocation. Such an electrophilic species can react with nucleophiles. A non-limiting example of such an iron(II) complex is ferrocyanide ([Fe $(CN)_6]^{4-}$). In this instance leaving group CN and ligand Z are the same group. Ferrocyanide is available from many commercial manufacturers, for example, Sigma Aldrich® (USA), as sodium ferrocyanide decahydrate ($[(CN)_6Fe]Na_4(H_2O)_{10}$). A non-limiting example of an iron containing catalyst, ferrocyanide, undergoing a reversible dissociation reaction is shown in equation (12) below.

$$[Fe(CN)_6]^{4-} \leftrightarrow [Fe(CN)_5]^{3-} + CN^- \qquad (12)$$

The iron containing catalyst can react with nucleophiles in the reaction mixture, for example, hydroxide ion as shown in equation (13) below.

$$[Fe(CN)_5]^{3-} + OH^- \leftrightarrow [Fe(CN)_5(OH)]^{4-} \qquad (13)$$

Without wishing to be bound by theory, it is believed that the $[Fe(CN)_5(OH)]^{4-}$ species is responsible for the reaction with small organic molecules (e.g., formaldehyde in either intact or hydrated form), followed by reductive elimination of hydrogen and consequent formation of the formate anion as shown in the reaction pathway (B) below. Alternatively, the partly deprotonated form of methanediol ($CH_2(OH)_2$), as obtained from the attack of hydroxide ion to p-formaldehyde, may also directly coordinate to the 16-electron [Fe$(CN)_5]^{3-}$ intermediate to form the same species as shown in reaction pathway (B) below, where Z is CN, a is +2, n is 5, and b is −5.

(B)

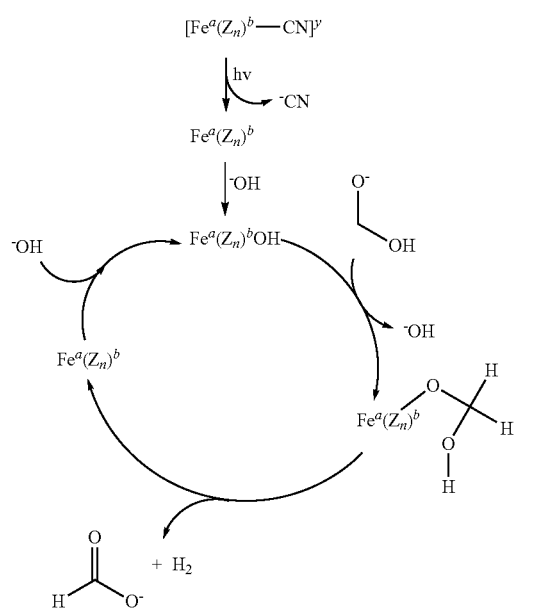

A non-limiting example of a transition metal complex undergoing a reversible dissociation reaction under basic pH is shown in reaction pathway (C) below. In a preferred embodiment, Z and L are halides.

(C)

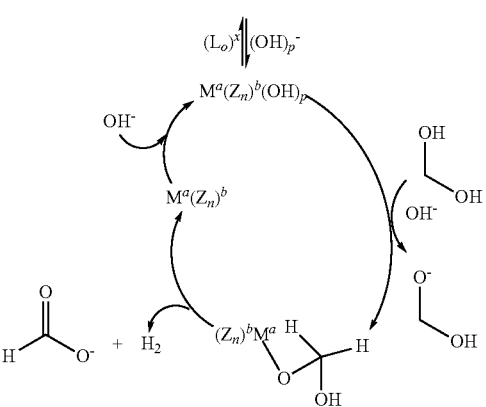

where M is a transition metal having a charge a, Z is a ligand bonded to the metal with a charge of b, L is a leaving group with a charge of x, and a is a positive integer from 0 to 6, preferably 0 to 3, b is an negative integer from 0 to −5, x is a negative integer from −1 to −2, y is the total charge of the transition metal complex, and n, o, and p are the atomic ratio relative to M, where n is 0 to 6, o is 1 to 3, p is 0 to 1, and y is 0, −1, −2, −3, −4, −5, or −6.

B. Reactants and Medium for Production of Hydrogen and Formate

1. Reactants

The reactants in the step of producing formate and $H_2$ can include formaldehyde, paraformaldehyde, or other organic molecules that release formaldehyde in aqueous solution. Formaldehyde can be formaldehyde, aqueous formaldehyde solutions (for example, 37% in water), para-formaldehyde, or combinations thereof. para-Formaldehyde is the polymerization of formaldehyde with a typical degree of polymerization of 1 to up to 100 units. Aqueous formaldehyde (methanediol) and para-formaldehyde are available from many commercial manufacturers, for example, Sigma Aldrich® (USA). In addition, reactants can include small organic molecules with a terminal aldehyde (RHCO), where R is H or an alkyl group having 1 to 3 carbons. The basic reagent can include a metal hydroxide (MOH or M(OH)$_2$), where M is a alkali or alkaline earth metal. Non-limiting examples of alkali or alkaline earth metals include lithium, sodium, potassium, magnesium, calcium, and barium. In a preferred embodiment, the base is sodium hydroxide (NaOH). The molar ratio of small organic molecule (e.g., formaldehyde) to base is equal to or less than 2:1, 1.9:1, 1.8:1, 1.7:1, 1.6:1, 1.5:1, 1.2:1, 1.1:1, 1:1, 0.5:1 or any range there between.

2. Medium

The production of hydrogen and formate from formaldehyde can be performed in any type of medium that can solubilize the catalyst and reagents. In a preferred embodiment, the medium is water. Non-limiting examples of water include de-ionized water, salt water, river water, canal water, city canal water or the like.

C. Generation of Hydrogen and Formate

Figure 1A:
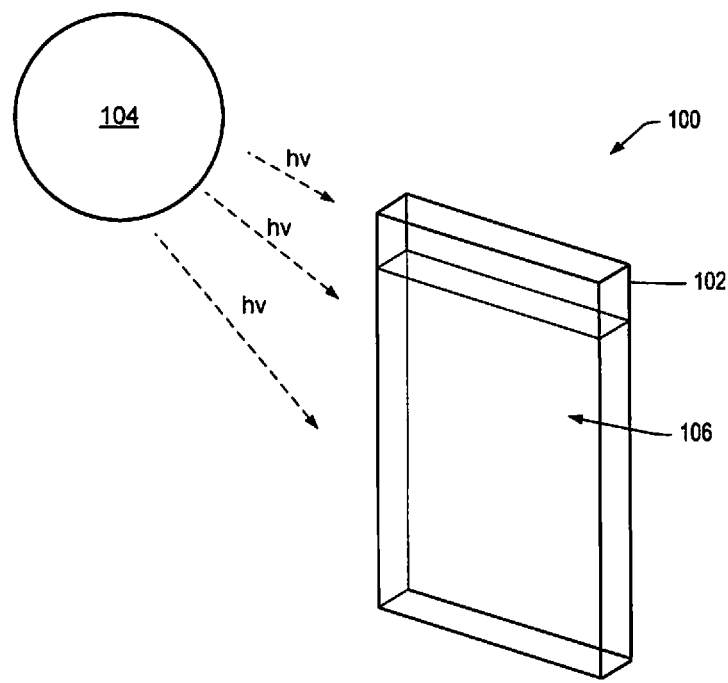
FIGS. 1A and 1B are schematics of embodiments of reaction systems of the present invention wherein light (A)

As illustrated in the Examples section, hydrogen and formate can be produced by irradiating, with light, an aqueous composition having a basic pH, formaldehyde, and a transition metal complex catalyst. In preferred instances, the catalyst and the formaldehyde are partially or fully solubilized within the aqueous composition. FIG. 1A is a schematic of an embodiment of a reaction system 100 for producing hydrogen and formate from formaldehyde. System 100 is particularly suited to methods that use a transition metal complex catalyst having a leaving group that dissociates from the transition metal complex in response to light. System 100 includes unit 102, light source 104, and aqueous mixture 106. Unit 102 can be transparent, translucent, or even opaque such as those that can magnify light (e.g., opaque container having a pinhole(s) or those that include a light source within the container). The aqueous homogeneous mixture 106 includes the aqueous formaldehyde (methanediol), a transition metal complex catalyst, and a base described throughout the specification. Light source 104 can be natural sunlight or an artificial light source such as light from a xenon lamp, a fluorescent light, a light emitting diode (LED), an incandescent light, an ultraviolet (UV) light, or any combination thereof. In certain instances, a combination of natural and artificial light can be used. The transition metal complex catalyst can be used to catalyze the production of formate and hydrogen from the formaldehyde as shown in reaction pathways (A) and (B) above. When the aqueous mixture 106 is exposed the light source 104, $H_2$ (gas) and formate are produced. Notably, formate and hydrogen are produced only when the solution containing the catalyst is exposed to light. No formate or hydrogen are produced when aqueous formaldehyde and sodium hydroxide solution alone are exposed to light. Thus, it should be understood that you can either illuminate and then add the catalyst or add the catalyst and then illuminate the solution.

Figure 1B:
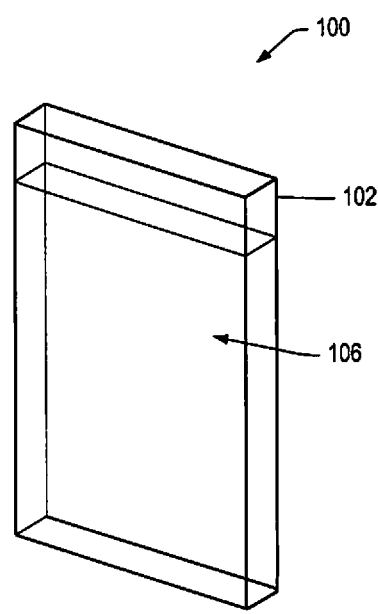

System 100 can also be used in embodiment when the leaving group dissociates in response to the basic pH of the solution (for example, as shown in pathway (C) above). System 100 is particularly suited to methods that use a transition metal complex catalyst having a leaving group that dissociates from the transition metal complex in response to pH. In such a system, system 100 light source 104 is not necessary. Said another way system 100 includes unit 102 and aqueous mixture 106 as shown in FIG. 1B.

When equimolar solutions of p-formaldehyde and sodium hydroxide are combined, a slow Cannizzaro's disproportionation to MeOH and (HCOO)Na can occur as shown in equation (14) below. The addition of a catalytic amount of the transition metal catalyst containing does not appear to inhibit this disproportionation.

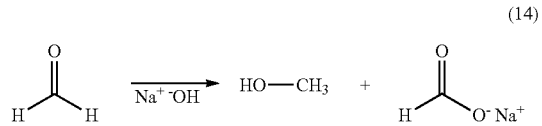

(14)

The production of formate (e.g., sodium formate) can be as illustrated in the reaction pathways (A), (B), and (C) above and equation (15) below.

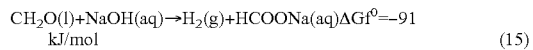

(15)

Without wishing to be bound by the theory, the production of hydrogen is in the homogeneous phase of the aqueous mixture. The spent transition metal complex (e.g., $(M)^a(Z_n)^b$) can be precipitate or be precipitated from the solution by addition of acid to increase the pH of the solution. The resulting precipitate can be removed, or substantially removed, through known solid/liquid filtration methods (e.g., centrifugation, filtration, gravity settling, etc.). In some embodiments, the transition metal complex is not removed or is partially removed from the solution. The formate (or formic acid), which is also dissolved in the solution, can then be used as a carbon source for production of calcium carbonate.

Notably, no carbon dioxide is formed during the production of formate and hydrogen. Thus, the process can be considered a "green" process. Furthermore, system 100 does not require the use of an external bias or voltage source, although one can be used if so desired. Further, the efficiency of system 100 allows for one to use formaldehyde as a hydrogen storage agent and formate as a carbon source.

D. Generation of Calcium Formate

In some embodiments, a step in the production of calcium carbonate from formaldehyde includes production of calcium formate from formate or a salt thereof by reacting the formate or salt thereof with calcium hydroxide ($Ca(OH)_2$) as shown in equation (16), using sodium formate as an example of a salt of formate.

(16)

This process can be performed by any appropriate method known to those of ordinary skill in the art. In a non-limiting example, a basic aqueous sodium formate solution (e.g., pH of 12 to 13) can be at room temperature (e.g., 15° C. and 30° C., preferably 20° C. to 25° C.). Calcium hydroxide can be added to the solution to convert sodium formate to calcium formate and NaOH. The NaOH can then be recycled and used in the overall reaction (See, e.g., reaction scheme A).

In some embodiments, calcium formate can also be produced from formate or a salt thereof by an ion exchange process, such as that described in U.S. Pat. No. 6,492,551. In this process, formate ions from any source, including sodium formate, are bound to an anion exchange material. Calcium formate can be eluted from the material by feeding a calcium salt of an anion that replaces the formate anion bound to the anion exchange material. The anion that replaces the formate can be, for example, chloride (Cl⁻), and the calcium salt can be calcium chloride ($CaCl_2$).

E. Generation of Calcium Carbonate and Formaldehyde

Calcium carbonate and formaldehyde can be produced from calcium formate by any appropriate method known to those of ordinary skill in the art. In a non-limiting example, this can be achieved by heating calcium formate to a temperature of approximately 250° C. to 350° C., preferably around 300° C. to produce calcium carbonate and formaldehyde as shown in equation (17).

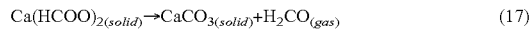

(17)

The formaldehyde gas can be captured and dissolved in water to be used in further production of hydrogen and calcium carbonate.

F. Methanol Feedstock

In some instances, methanol can be used as a feedstock for the production of hydrogen and calcium carbonate. Methanol can be oxidized to form formaldehyde by, for example, the Formox® (Formox AB, Sweden) process. In this process, methanol and oxygen react in the presence of a catalyst such as silver metal or a mixture of an iron oxide with molybdenum and/or vanadium to form formaldehyde. When the catalyst is a mixture of iron oxide with molybdenum and/or vanadium, methanol and oxygen react at about 300 to 400° C. to produce formaldehyde according to equation (18) below:

(18)

The formaldehyde can then be used as described above in the production of hydrogen and calcium carbonate.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Materials and Testing Procedures for Production of Hydrogen from Formaldehyde Materials. Paraformaldehyde, 37% formaldehyde solution, and sodium ferrocyanide decahydrate, acetamide were purchased from Sigma-Aldrich® (USA). Formic acid was purchased from Acros Organics (BELGIUM). Sodium thiosulfate was purchased from Oakwood Chemicals (USA). Iodine was purchased from Strem Chemicals, Inc. (USA). Citric acid was purchased from Fisher Scientific (USA). Acetic anhydride was purchased from VWR International (USA). Chemicals were used without further purification. If not specifically mentioned, all reactions were carried out in distilled water without degassing or other modifications.

Analytical Equipment. pH measurements were taken with a Hanna HI 2210 benchtop pH meter with a general purpose combination pH electrode, both purchased from Sigma-Aldrich®. Powder XRD diffractograms were obtained on a Rigaku Ultima IV diffractometer set to 2 2θo/min from 10-70 2θo. UV-Vis spectra were obtained on a Specmate UV-1100 spectrometer. Infrared spectra were obtained on a Nicolet 6700 FTIR with diamond ATR between 650-4000 $cm^{-1}$, at 128 scans with a resolution of 4 $cm^{-1}$.

Product Analysis. $H_2$, $CO_2$, CO and $O_2$ gas identification and detection was carried out with an Agilent 7820A GC equipped with a thermal conductivity detector (TCD), using an Agilent GS-CarbonPlot column (for $CO_2$) or Agilent HP-Molesieve column (for all other gasses).

Determination of Reaction Kinetics. The gaseous outflow of the reaction mixture was hooked up to a Restek Pro-FLOW 6000 Electronic Flow-meter connected to a computer.

Determination of pH. Two identical solutions of 66.6 mmol of p-formaldehyde and 375 mmol of NaOH were prepared simultaneously and were measured to have identical pH values. Both solutions were then illuminated and to one solution, 2 mmol of sodium ferrocyanide was added, and the pH values were measured at regular intervals for 300 minutes.

Determination of Formate Concentration. Concentration of dissolved formate was determined according to a modified colorimetric procedure by Sleat et al. (*Appl. Environ. Microbiol.* 1984, 47, 884). An aliquot of the reaction mixture (0.5 mL) was added to acetamide (10%, 2 mL) and citric acid (0.05%) dissolved in a 1:1 mixture of isopropanol and water. To the test mixture, sodium acetate (0.1 mL of 30%) and of acetic anhydride (7 mL) were added. The test mixture was shaken and incubated at room temperature for 60 minutes and measured spectrophotometrically at 510 nm. The concentration was determined against a standard curve.

Determination of Formaldehyde Concentration. Formaldehyde concentrations were determined through iodine/sodium thiosulfate titrations. To an aliquot of the reaction mixture (10 mL), de-ionized water (20 mL), iodine (25 mL, 0.05M/L in methanol) and sodium hydroxide (10 mL, 1.0M) were added and stirred for 10 minutes followed by the addition of sulfuric acid (15 mL, 1.0M). The sample solution was then titrated with sodium thiosulphate, with addition of a 1% starch solution as an indicator once the solution turned light yellow. The concentration of formaldehyde was then calculated by a standard curve.

Isolation of Iron Oxide. Iron oxide was collected after allowing a standard reaction to continue for 5 days with a continuous addition of para-formaldehyde and sodium hydroxide. A brown-red precipitate slowly formed which was centrifuged, washed and dried.

Example 2

Generation of Hydrogen and Formate from Para-Formaldehyde

Formaldehyde (50 mmol of p-formaldehyde or 37% formaldehyde solutions) was added to NaOH (250 mmol) in $H_2O$. The photocatalyst, sodium ferrocyanide ($[(CN)_6Fe]Na_4(H_2O)_{10}$), (500 µmol (1 mol %)) was added to the solution. The reaction mixture was illuminated with a 300 W Xe arc-lamp and the evolution of hydrogen was monitored. In this experiment 825 mL of hydrogen was generated over a 300 minute time period. The disappearance of formaldehyde was monitored by the titration method described above, while the formation of sodium formate was monitored by the colorimetric method described above. FIG. 2 are graphs of formation of products versus reagent consumption during irradiation. Data 202 is the amount of formaldehyde over time. Data 204 is the amount formate formed over time, and data 206 is the amount of hydrogen produced over time. As shown in FIG. 2, hydrogen and formate were both produced, which indicated that formaldehyde and hydroxide ion were both consumed in the reaction process.

Example 3

Catalytic Versus Non-Catalytic Generation of Hydrogen from Formaldehyde

Non-Catalyzed Procedure. Formaldehyde (66.6 mmol of p-formaldehyde) was added to NaOH (375 mmol) in $H_2O$. The reaction mixture was illuminated with a 300 W Xe arc-lamp. The change in pH was measured. No hydrogen evolution was detected. No catalyst was added to this solution.

Catalyzed Procedure. Formaldehyde (66.6 mmol of p-formaldehyde) was added to NaOH (375 mmol) in $H_2O$. The photocatalyst, sodium ferrocyanide ($[(CN)_6Fe]Na_4(H_2O)_{10}$), (2 mmol) was added to the solution (total volume 300 mL). The reaction mixture was illuminated with a 300 W Xe arc-lamp, the evolution of hydrogen was monitored, and the change in pH was measured.

FIG. 3 are graphs of the change of pH of the non-catalyzed reaction and the catalyzed reaction over time. Data 302 is the non-catalyzed reaction ("blank"). Data 304 is the catalyzed reaction. Data 306 is the hydrogen production from the catalyzed reaction. As shown in FIG. 3, the pH in both a catalyzed standard $H_2$ evolving reaction and a non-catalyzed reaction decrease over time. The pH of the catalyzed reaction had a faster rate with respect to $H_2$ production versus the non-catalyzed reaction (time 0 until no more hydrogen evolution was detected, about 30 min, See, FIG. 3), but over time the rate of pH change of the catalyzed reaction became similar to the rate of pH change of the non-catalyzed reaction. Without wishing to be bound by theory it is believed that decrease in the pH after no more hydrogen evolution was detected (about 30 min.) is due to the Cannizzaro reaction (See, equation 11). In addition, without wishing to be bound by theory, it is believed that the initial rate of pH change at the beginning of the catalyzed reaction indicated that hydroxide ion is also required to activate the catalyst.

Example 4

Variation of Formaldehyde Concentration p-Formaldehyde in the amounts listed in Table 1 were added to NaOH (375 mmol) in $H_2O$. The photocatalyst, sodium ferrocyanide ($[(CN)_6Fe]Na_4(H_2O)_{10}$), (0.5 mmol) was added to the solution (total volume 250 mL). The amount of hydrogen evolution was measured. The reaction mixture was illuminated with a 300 W Xe arc-lamp and the evolution of hydrogen was monitored. FIG. 4 is a graph of the change of hydrogen evolution versus the amount of p-formaldehyde added at a constant amount of NaOH. From the data in FIG. 4, at low initial concentrations of p-formaldehyde, the conversion to hydrogen was deemed to be as high as 100%, but decreased when the concentration levels of the p-formaldehyde increased. The maximum total productivity was reached when the amount of p-formaldehyde was approximately equimolar with NaOH (p-formaldehyde/NaOH=1.2). At higher ratios hydrogen production was not as pronounced.

p-Formaldehyde in concentrations listed in Table 1 was added to 300 mL of 1.125 M NaOH (about 0.34 mmol) in $H_2O$. The photocatalyst, sodium ferrocyanide ($[(CN)_6Fe]Na_4(H_2O)_{10}$), (0.6 mmol) was added to the solution and the evolution of hydrogen was monitored. The reaction mixture was illuminated with a 300 W Xe arc-lamp. The amount of hydrogen evolution was measured. Table 1 is a listing of the amount of hydrogen evolved and the catalyst turnover.

TABLE 1

| Formaldehyde (mmoles) | Hydrogen evolved (mmoles) | Yield (%) | Turnovers |
|---|---|---|---|
| 0.33* | 0.33 | 100% | 0.56 |
| 3.33* | 3.15 | 94% | 5.25 |
| 6.67* | 5.23 | 78% | 8.72 |
| 33.33* | 19.62 | 59% | 32.70 |
| 66.67* | 34.13 | 51% | 56.88 |
| 333.33* | 69.90 | 21% | 116.49 |
| 375.00** | 59.35 | 16% | 98.92 |

*Commercial para-formaldehyde.
**Commercial Formalin solution.

Example 5

(Effect of Radiation)

Formaldehyde (66.6 mmol, p-formaldehyde) was added to NaOH (325 mmol) in $H_2O$. The photocatalyst, sodium ferrocyanide ($[(CN)_6Fe]Na_4(H_2O)_{10}$), (2 mmol) was added to the solution (total volume 300 mL). The reaction mixture was illuminated with a 300 W Xe arc-lamp and the evolution of hydrogen was monitored. FIG. 5 is a graph of the effect of illumination on hydrogen evolution from ferrocyanide catalysis over time. The portion of the lines that have a slope (data 502, Δ) represents periods when catalyst is illuminated and the substantially flat portions of the line (data 504,●) represents periods when catalyst is in the dark. From the data in FIG. 5, it was determined that when irradiation with visible light was interrupted, the hydrogen evolution stopped and it was either restarted or arrested by intermittently turning the light on and off. In other words, in some instances, the catalytic system of the present invention is light-switchable.

Example 6

Hydrogen Rate of Formation and Production

Formaldehyde (50 mmol of p-formaldehyde) was added to NaOH (250 mmol) in $H_2O$. The photocatalyst, sodium ferrocyanide ($[(CN)_6Fe]Na_4(H_2O)_{10}$), (0.5 mmol) was added to the solution (total volume 300 mL). The reaction mixture was illuminated with a 300 W Xe arc-lamp and the evolution of hydrogen was monitored. An initial 0.25 moles of NaOH was added to both solutions to ensure that the pH was suitable for deprotonation of methanediol. Every 30 minutes, 50 mmol p-formaldehyde and either 50 mmol or 200 mmol NaOH were added. The hydrogen rate of formation (FIG. 6) and productivity (FIG. 7) were monitored by regularly adding p-formaldehyde and NaOH in both a 1:5 and 1:1 molar ratio. FIG. 6 are graphs of the hydrogen flow in ml/min versus time in minutes at various p-formaldehyde and NaOH concentrations. Data 602 is at 50 mmol of NaOH and data 604 is at 200 mmol of NaOH. FIG. 7 are graphs of the hydrogen production versus time in minutes at various p-formaldehyde and NaOH concentrations. Data 702 is at 50 mmol of NaOH and data 704 is at 200 mmol of NaOH. Elevated hydrogen evolution rates were observed when the ratio of p-formaldehyde to NaOH was 1:5, which slowed before the next sample was added. However, with each addition of p-formaldehyde and NaOH, the maximum rate decreased rapidly and after the $10^{th}$ addition of regents, the rate was zero. This drop was attributed to decomposition of the catalyst to $Fe_2O_3$ in highly basic conditions. As shown in FIG. 7, addition of 1:1 p-formaldehyde to NaOH portions (data 602) resulted in a steady productivity being reached, with no decline of catalytic activity for 350 minutes. Within each addition, a reduction in the initial spike of hydrogen production is observed, which stabilizes into a nearly continuous release of 10 mL of hydrogen per minute.

Example 7

Effect of Water Purity on Catalytic Activity

Formaldehyde (66.6 mmol of p-formaldehyde) was added to NaOH (375 mmol) in $H_2O$. The photocatalyst, sodium ferrocyanide ($[(CN)_6Fe]Na_4(H_2O)_{10}$), (3 mmol) was added to the solution (total volume 300 mL). Three types of water de-ionized water, river water and salt water were evaluated. FIG. 8 are graphs of hydrogen production in mL versus time in min of the production of hydrogen using various types of water. Data 802 is hydrogen production using de-ionized water, data 804 is hydrogen production using city canal water, and data 806 is hydrogen production using salt water. As determined from the data in FIG. 8, the reaction rates and final production from the three sources were nearly identical. Thus, the choice of water source (i.e., distilled water, 3.5% NaCl solutions (to match the average salinity of the ocean), or water taken directly from city canal water), had no significant effect on the activity of the catalyst.

Example 8

Long Range Catalytic Runs

Formaldehyde (0.5 mol of p-formaldehyde) was added to NaOH (0.25 mol) in $H_2O$. The sodium ferrocyanide photocatalyst ($[(CN)_6Fe]Na_4(H_2O)_{10}$, 120 mg) was added to the solution (total volume 300 mL). The reaction mixture was run twice with two different light sources, a 300 W Xe arc-lamp and a Hg lamp. The evolution of hydrogen was monitored. FIG. 9 are graphs of hydrogen evolution versus time using different light sources. Data 902 is the generation of hydrogen using an embodiment of the present invention using a Xenon arc-lamp as a light source. Data 904 is the generation of hydrogen using an embodiment of the present invention using the Hg lamp as a light source. From the data in FIG. 9, it was determined that the reactions were uninterruptedly carried out for 16 h with periodical additions of NaOH/p-formaldehyde every 30 min. Over time the catalytic system slowly decayed after having produced about 4.8 L of pure hydrogen (14.5% based on p-formaldehyde). At this stage a significant amount of $Fe_2O_3$ become visible, which was isolated and characterized as described in Example 1.

The invention claimed is:

1. A method of producing hydrogen and calcium carbonate, the method comprising:
    (a) combining an aqueous base, formaldehyde, and a transition metal complex having a coordination bond between a transition metal and a leaving group to form a homogeneous aqueous solution having a basic pH, wherein the leaving group dissociates from the transition metal complex in response to light and/or the basic pH of the solution;
    (b) producing hydrogen ($H_2$) gas and formate or a salt thereof from the formaldehyde present in the homogeneous aqueous solution; and
    (c) producing $CaCO_3$ using the formate or salt thereof as a carbon source.

2. The method of claim 1, wherein step (c) comprises:
    producing calcium formate ($Ca(HCOO)_2$) by reacting the formate or salt thereof with calcium hydroxide ($Ca(OH)_2$); and
    (ii) producing $CaCO_3$ and formaldehyde from the $Ca(HCOO)_2$.

3. The method of claim 2, wherein aqueous base is produced in step (c)(i) and recycled and used in steps (a) and (b).

4. The method of claim 2, wherein the formaldehyde from step (c)(ii) is recycled and used in steps (a) and (b).

5. The method of claim 1, wherein steps (a) and/or (b) are each performed at a temperature from greater than 0° C. to less than 50° C.

6. The method of claim 1, wherein a hydroxide ion replaces the leaving group to form a transition metal-hydroxyl coordination bond, and wherein the transition metal complex having the transition metal-hydroxyl coordination bond reacts with the formaldehyde to produce hydrogen and formate or salt thereof.

7. The method of claim 6, wherein the transition metal complex is an Fe complex, or an Fe(II) complex.

8. The method of claim 6, wherein the transition metal complex is a Ru complex, or a Ru(III) complex.

9. The method of claim 6, wherein the transition metal complex is an Ir complex, or an Ir(III) complex.

10. The method of claim 6, wherein the transition metal complex is a Cu complex, or a Cu(I) complex.

11. The method of claim 6, wherein the transition metal complex is an Ag complex, or an Ag(I) complex.

12. The method of claim 1, wherein the leaving group dissociates from the transition metal complex in response to light.

13. The method of claim 12, wherein the leaving group is a cyano group ($CN^-$).

14. The method of claim 13, wherein the transition metal complex is ferricyanide ($Fe(CN)_6)^{4-}$) or a salt thereof.

15. The method of claim 1, wherein the leaving group dissociates from the transition metal in response to the basic pH of the solution.

16. The method claim 1, wherein the leaving group is chloride ($Cl^-$), fluoride ($F^-$), bromide ($Br^-$), iodide ($I^-$), or astatide ($At^-$).

17. The method of claim 1, wherein the molar ratio of formaldehyde to base is equal to or less than 2:1.

18. The method of claim 1, wherein the homogeneous aqueous solution has a pH from 8 to 14.

19. The method of claim 1, wherein the formaldehyde and the transition metal complex are fully solubilized in the homogeneous aqueous solution.

* * * * *

UNITED STATES PATENT AND TRADEMARK OFFICE
CERTIFICATE OF CORRECTION

PATENT NO. : 10,183,864 B2
APPLICATION NO. : 15/503510
DATED : January 22, 2019
INVENTOR(S) : Balamurugan Vidjayacoumar and Khalid Al-Bahily It is certified that error appears in the above-identified patent and that said Letters Patent is hereby corrected as shown below:

In the Claims

On Column 22, Line 37: "$(Cr^-)$" should read --$(Cl^-)$--.

Signed and Sealed this
Ninth Day of April, 2019

Andrei Iancu
*Director of the United States Patent and Trademark Office*